(12) United States Patent
Velhal et al.

(10) Patent No.: US 8,440,223 B2
(45) Date of Patent: May 14, 2013

(54) SUSTAINED RELEASE PHARMACEUTICAL COMPOSITIONS COMPRISING QUETIAPINE IN NON-GELLABLE POLYMERS

(75) Inventors: Avinash Krishnaji Velhal, Pune (IN); Sunil Anantrao Mirajkar, Pune (IN); Virendra Ramkrupal Kuril, Pune (IN); Vineeth Raghavan, Pune (IN); Ninad Deshpanday, Pune (IN)

(73) Assignee: Lupin Limited, Mumbai, Maharashtra (IN)

( * ) Notice: Subject to any disclaimer, the term of this patent is extended or adjusted under 35 U.S.C. 154(b) by 106 days.

(21) Appl. No.: 13/002,277

(22) PCT Filed: Jun. 29, 2009

(86) PCT No.: PCT/IN2009/000369
§ 371 (c)(1),
(2), (4) Date: Feb. 3, 2011

(87) PCT Pub. No.: WO2010/001413
PCT Pub. Date: Jan. 7, 2010

(65) Prior Publication Data
US 2011/0151002 A1    Jun. 23, 2011

(30) Foreign Application Priority Data
Jul. 1, 2008    (IN) .......................... 1143/KOL/2008

(51) Int. Cl.
*A61K 9/14*    (2006.01)
*A61K 9/20*    (2006.01)
*A61K 9/48*    (2006.01)

(52) U.S. Cl.
USPC ............................ 424/451; 424/464; 424/489

(58) Field of Classification Search .................. None
See application file for complete search history.

(56) References Cited

U.S. PATENT DOCUMENTS

| | | | |
|---|---|---|---|
| 4,879,288 A | | 11/1989 | Warawa et al. |
| 5,948,437 A | * | 9/1999 | Parikh et al. .................. 424/464 |
| 2005/0158383 A1 | | 7/2005 | Boehm et al. |

FOREIGN PATENT DOCUMENTS

| WO | WO 2007/000778 A2 | 1/2007 |
|---|---|---|
| WO | WO 2007/133583 A2 | 11/2007 |
| WO | WO 2008/090569 A1 | 7/2008 |
| WO | WO 2010/012490 A1 | 2/2010 |

OTHER PUBLICATIONS

Form PCT/IB/326 for corresponding International Application PCT/IN2009/000369.
Form PCT/IB/373 for corresponding International Application PCT/IN2009/000369.
Form PCT/ISA/237 for corresponding International Application PCT/IN2009/000369.

* cited by examiner

Primary Examiner — Carlos Azpuru
(74) Attorney, Agent, or Firm — Merchant & Gould P.C.

(57) ABSTRACT

A sustained release dosage form comprising Quetiapine or a pharmaceutically acceptable salt, polymorphs, solvates, hydrates thereof and one or more non-gellable release controlling polymer and one or more pharmaceutically acceptable excipient(s). A sustained release dosage form comprising first granulation comprising Quetiapine or its pharmaceutically acceptable salts, polymorphs, solvates, hydrates thereof and one or more release controlling material; and second granulation comprising one or more release controlling material which is the same or different than the one or more release controlling material of the first granulation and optionally quetiapine or its pharmaceutically acceptable salts, polymorphs, solvates, hydrates thereof. A method of preparing the sustained release dosage form by first and second granulation followed by milling; blending the said milled granules after second granulation with lubricant followed by compression to form a sustained release dosage form. A sustained release dosage form comprising immediate release core comprising Quetiapine or a pharmaceutically acceptable salt, polymorphs, solvates, hydrates thereof and one or more pharmaceutically acceptable excipients; and sustained release coating comprising one or more non-gellable release controlling material.

5 Claims, No Drawings

SUSTAINED RELEASE PHARMACEUTICAL COMPOSITIONS COMPRISING QUETIAPINE IN NON-GELLABLE POLYMERS

This application is a National Stage Application of PCT/IN2009/000369, filed Jun. 29, 2009, which claims benefit of Serial No. 1143/KOL/2008, filed Jul. 1, 2008 in India and which application(s) are incorporated herein by reference. To the extent appropriate, a claim of priority is made to each of the above disclosed applications.

FIELD OF THE INVENTION

The present invention relates to a sustained release dosage form comprising Quetiapine or a pharmaceutically acceptable salt(s), polymorphs, solvates, hydrates thereof and process for its preparation.

BACKGROUND OF THE INVENTION

Quetiapine and its salts, particularly Quetiapine hemifumarate, have been employed as pharmaceutically active agents in the treatment of schizophrenia and bipolar mania.

Quetiapine fumarate is a psychotropic agent belonging to a chemical class of dibenzothiazepine derivatives. The chemical designation is 2-[2-(4-dibenzo[V][1,4]thiazepin-11-yl-1-piperazinyl)ethoxy]-ethanol fumarate (2:1) (salt). It is present in tablets as the fumarate salt.

U.S. Pat. No. 4,879,288 disclose the product Quetiapine and its pharmaceutically acceptable salt(s) along with preparation process.

Dosing regimens for antipsychotics is generally two or three tablets per day. These dosing regimens have proved disadvantageous because of lack of convenience, and more importantly, lack of compliance. Control of Quetiapine plasma levels is useful during treatment. For example, when a patient presents with acute psychosis, it may be desirable to introduce an immediate large dosage of Quetiapine, followed by the maintenance of sustained plasma level of Quetiapine. Single dosage forms that provide particular plasma profiles of Quetiapine are thus desirable. Many techniques have been used to provide sustained release pharmaceutical dosage forms in order to maintain therapeutic serum levels of medicaments and to minimize the effects of missed doses of drugs caused due to lack of patient compliance.

It is typically the goal of all sustained-release preparations to provide a longer period of pharmacological response after the administration of the dosage form than that which is ordinarily experienced after the administration of the immediate release dosage forms. Desirably the sustained release provides a generally uniform and constant rate of release over an extended period of time, which achieves a stable and desired blood (plasma) level of the active ingredient without the need for frequent administration of the medicament.

However, it is often not possible to readily predict whether a particular sustained release formulation will provide the desired sustained release of a relatively sparingly soluble to insoluble drug, and it has generally been found that it is necessary to carry out considerable experimentation to obtain sustained release formulations of such drugs having the desired bioavailability when ingested.

U.S. Pat. No. 5,948,437 disclose sustained release formulation of Quetiapine and its salt using gelling agents.

US 2005158383 is related to a dual retard solid dosage formulation comprising a matrix comprising a therapeutically effective amount of Quetiapine or a pharmaceutically acceptable salt thereof; and a wax material.

WO 2007/133583 A2 is related to a zero order modified release dosage form having a matrix core comprising hydrophobic agent, which acts as a release retardant and a modified release coating.

The recommended initial dose is 300 mg/day. Patients should be titrated within a dose range of 400-800 mg/day depending on the response and tolerance of the individual patient. Dose increases can be made at intervals as short as 1 day and increments of up to 300 mg/day.

For some patients, the Quetiapine dosage required for therapeutic effect is quite high, especially if a sustained release dosage form is administered. For example, the largest current dosage form is a 300 mg tablet, administered two or three times daily. Thus an equivalent once a day dosage form would contain high amount of Quetiapine.

When a high dosage of Quetiapine is combined with excipients, the resulting dosage form (e.g., tablets, capsules, etc.) may be considerably larger than is desirable. Also, the dosage form can be undesirably large when Quetiapine is combined with other active agents, especially other high dose active agents. The large size of these dosage forms can be difficult for patients, especially elderly patients, to swallow. Further, large dosage form size may increase the risk of choking upon oral administration and may reduce patient compliance.

Thus there exists a need for a dosage form comprising a high dose amount of Quetiapine that has a smaller size than the conventional dosage forms containing substantially the same dose amount of Quetiapine.

The present invention addresses these and other needs for improved Quetiapine dosage forms, particularly controlled release and/or sustained release dosage forms. The present invention relates to a pharmaceutical composition and more particularly to a sustained release pharmaceutical composition comprising Quetiapine or a pharmaceutically acceptable salt thereof.

OBJECTS OF THE INVENTION

It is an object of the present invention to provide a sustained release dosage form comprising matrix comprising Quetiapine or a pharmaceutically acceptable salt, polymorphs, solvates, hydrates thereof and one or more non-gellable release controlling polymer and one or more pharmaceutically acceptable excipient(s) thereof.

Another object of the present invention to provide a sustained release dosage form comprising: a first granulation comprising Quetiapine or its pharmaceutically acceptable salts, polymorphs, solvates, hydrates thereof and one or more release controlling material; and a second granulation comprising one or more release controlling material which is the same or different than the one or more release controlling material of the first granulation and optionally quetiapine or its pharmaceutically acceptable salts, polymorphs, solvates, hydrates thereof.

Another object of the present invention to provide a method of preparing a sustained release dosage form comprising: first granulation comprising Quetiapine or its pharmaceutically acceptable salts, polymorphs, solvates, hydrates thereof and one or more release controlling material followed by milling; and second granulation using milled granules of first granulation and one or more release controlling material which is the same or different than the one or more release controlling material of the first granulation followed by milling; blending the said milled granules after second granulation with lubricant followed by compression to form a sustained release dosage form.

Another object of the present invention to provide a sustained release dosage form comprising: immediate release matrix comprising Quetiapine or a pharmaceutically acceptable salt, polymorphs, solvates, hydrates thereof and one or more pharmaceutically acceptable excipients; and sustained release coating comprising one or more release controlling material.

Another object of the present invention to provide a sustained release dosage form comprising an active agent Quetiapine or a pharmaceutically acceptable salt, polymorphs, solvates, hydrates thereof; wherein the active agent is present in an amount of more than 40% by weight of the total weight of the core.

Yet another object of the present invention to provide a sustained release dosage form comprising a first granulation comprising Quetiapine or its pharmaceutically acceptable salts, polymorphs, solvates, hydrates thereof and one or more release controlling material; and a second granulation comprising one or more release controlling material which is the same or different than the one or more release controlling material of the first granulation; wherein Quetiapine is present in an amount of more than 40% by weight of the total weight of the core.

DETAILED DESCRIPTION OF THE INVENTION

In accordance with the above-mentioned objects and others, the present invention in certain embodiments is directed to a sustained release Quetiapine dosage form comprises a matrix, wherein the matrix comprises a pharmaceutically effective amount of Quetiapine and a non-gellable release controlling polymer.

The non-gellable release controlling polymer is selected from, but not limited to, cellulose acetate, acrylic polymer such as Poly (ethyl acrylate, methyl methacrylate) polymer e.g. Eudragit NE 30D®, ammonioalkyl methacrylate copolymers e.g. Eudragit RL/RS® etc.

In another aspect, the present invention is directed to a sustained release solid oral dosage form comprising a multigranular formulation, preferably a bigranular formulation with Quetiapine or a pharmaceutically acceptable salt, polymorphs, solvates, hydrates (hereinafter referred as Quetiapine) thereof in the granulation.

Preferably, the dosage form comprises a first granulation comprising one or more release controlling material and Quetiapine and a second granulation comprising one or more controlling material, which is the same, or different than the one or more release controlling material of said first granulation and optionally quetiapine or its pharmaceutically acceptable salts, polymorphs, solvates, hydrates thereof.

The release rate of the drug from the dosage form can be sustained by adjusting the ratio of the two granulations.

In certain embodiments the present invention is directed to a sustained release dosage form comprising: a normal release matrix comprising Quetiapine and one or more pharmaceutically acceptable excipient(s); and a sustained release coating comprising one or more release controlling material.

In yet another embodiment the present invention is directed to a sustained release dosage form comprising an active agent Quetiapine, and one or more release controlling material, wherein the active agent is present in an amount of more than 40% by weight of the total weight of the core.

In another embodiment the present invention is directed to sustained release dosage form wherein the dosage form can be bilayered compositions having drug i.e. quetiapine fumarate in one or both layers. Both layers may have sustained release or one layer has immediate release and the other sustained.

Further the dosage form can have drug comprising beads or pellets having similar or different release profiles.

The term "active agent" "drug" "active" can be interchangeably used.

The term "sustained release" refers to any composition or dosage form, which is other than immediate release such as extended release", "sustained release", "controlled release", "pulsatile release" "timed release" "programmed release" "delayed release" and/or "rate controlled" compositions or dosage forms.

The term "core" encompasses the drug Quetiapine as defined, one or more pharmaceutically acceptable excipients optionally one or more release controlling material.

The dosage forms of the present invention may further comprise pharmaceutically acceptable excipients known in the art. These include but are not limited to binders, lubricants, glidants, fillers, diluents and the like.

The amounts of additive employed will depend upon how much active agent is to be used. One excipient can perform more than one function.

Binders include, but are not limited to, microcrystalline cellulose such as products known under the registered trade marks Avicel, Filtrak, Heweten or Pharmacel.

Lubricants may be selected from, but are not limited to, those conventionally known in the art such as Magnesium, Aluminium or Calcium or Zinc stearate, polyethylene glycol, glyceryl behenate, mineral oil, sodium stearyl fumarate, stearic acid, hydrogenated vegetable oil and talc.

Glidants include, but are not limited to, silicon dioxide; magnesium trisilicate, powdered cellulose, starch, talc and tribasic calcium phosphate.

Fillers or diluents, which include, but are not limited to confectioner's sugar, compressible sugar, dextrates, dextrin, dextrose, fructose, lactitol, mannitol, sucrose, starch, lactose, xylitol, sorbitol, talc, microcrystalline cellulose, calcium carbonate, calcium phosphate dibasic or tribasic, calcium sulphate, and the like can be used.

One or more of these additives can be selected and used by the skilled artisan having regard to the particular desired properties of the solid oral dosage form. The amount of each type of additive employed, e.g. glidant, binder, disintegrant, filler or diluent and lubricant may vary within ranges conventional in the art.

The sustained release dosage form of the invention, wherein the core can be formed by various methods known in the art.

In certain embodiments, the present invention is further directed to a method of preparing a sustained release dosage form as described herein.

a) first granulation comprising Quetiapine and one or more release controlling material
b) followed by milling
c) second granulation using milled granules of first granulation and one or more release controlling material
d) followed by milling;
e) blending the said milled granules after second granulation with lubricant
f) followed by compression to form a sustained release dosage form.

Alternatively, the blend of step e is filled into capsules.

The tablets were further coated by using any of the conventional coating techniques, such as pan or perforated pan, well known to the persons skilled in the art.

These coating layers comprise of one or more excipients selected from the group comprising coating agents, opacifiers, taste-masking agents, colouring agents, antitacking agents and the like.

Coating agents which are useful in the coating process, include, but are not limited to, polymers based on methacrylic acid such as Poly(butyl methacrylate, (2-dimethylaminoethyl) methacrylate, methyl methacrylate) copolymer for e.g. those marketed under the brand name of Eudragit. These may be applied from aqueous or non-aqueous systems or combinations of aqueous and non-aqueous systems as appropriate.

Additives can be included along with the film formers to obtain satisfactory films. These additives can include plasticizers such as dibutyl phthalate, triethyl citrate, polyethylene glycol and the like, antitacking agents such as talc, stearic acid, magnesium stearate and colloidal silicon dioxide and the like, surfactants such as polysorbates and sodium lauryl sulphate and opacifying agents such as titanium dioxide and the like. All these excipients can be used at levels well known to the persons skilled in the art.

The following are non-limiting examples, which serve to illustrate the invention.

EXAMPLES

Example 1

| Ingredients | Qty (% wt) |
| --- | --- |
| Quetiapine Fumarate | 57.5 |
| Lactose | 2-10 |
| Sodium Citrate | 2-10 |
| Methacrylate copolymer | 5-20 |
| Cellulose Acetate | 1-10 |
| Lactose | 5-30 |
| Talc | 0.5-3.0 |
| Magnesium stearate | 0.5-3.0 |

Quetiapine Fumarate, sodium citrate and lactose were sifted and uniformly mixed. The blend was granulated with Ammonio methacrylate copolymer dispersion. The granules so formed were dried, milled and sifted through #40 mesh. The above granulate was further granulated with cellulose acetate solution. The granules so formed were dried, milled and sifted through #20 mesh. These granules were uniformly mixed with remaining amount of lactose, talc and magnesium stearate. The blend was compressed into tablets using suitable punch. The tablets were then further film coated.

Example 2

| Ingredients | Qty (% wt) |
| --- | --- |
| Quetiapine Fumarate | 57.5 |
| Trisodium citrate dihydrate | 2.5-10 |
| Lactose | 5-30 |
| Methacrylate copolymer | 2-20 |
| Cellulose acetate | 2-15 |
| Talc | 0.5-3 |
| Magnesium stearate | 0.5-3 |

Example 3

| Ingredients | Qty (% wt) |
| --- | --- |
| Quetiapine Fumarate | 57.5 |
| Trisodium citrate dihydrate | 2.5-10 |
| Lactose | 5-30 |
| Methacrylate copolymer | 2-20 |
| Cellulose acetate | 2-15 |
| Talc | 0.5-3 |
| Magnesium stearate | 0.5-3 |

Examples 2 and 3 were prepared as given in example 1.

Example 4

| Ingredients | Qty (% wt) |
| --- | --- |
| Quetiapine Fumarate | 50.75 |
| Trisodium citrate dihydrate | 2.5-10 |
| Sodium chloride | 2-10 |
| Mannitol | 5-50 |
| Microcrystalline cellulose | 2-15 |
| Talc | 0.5-3 |
| Magnesium stearate | 0.5-3 |
| Cellulose Acetate | 1-10 |

Quetiapine Fumarate, trisodium citrate dihydrate, sodium chloride, dicalcium phosphate dihydrate and lactose were sifted and uniformly mixed. The above blend was wet granulated and the granules were dried, milled and sifted. The granules were lubricated with talc and magnesium stearate and core tablets are compressed using suitable punch. The core tablets were coated with a solution of cellulose acetate.

Example 5

| Ingredients | Qty (% wt) |
| --- | --- |
| Quetiapine Fumarate | 63.19 |
| Trisodium citrate dihydrate | 1-10 |
| Dicalcium phosphate dihydrate | 5-25 |
| Lactose | 5-50 |
| Talc | 0.25-3 |
| Magnesium stearate | 0.5-3 |
| Methacrylate copolymer | 0.5-10 |
| Talc | 0.25-10 |

Quetiapine Fumarate, trisodium citrate dihydrate, dicalcium phosphate dihydrate and lactose were sifted and uniformly mixed. The above blend was wet granulated and the granules were dried, milled and sifted. The granules were lubricated with talc and magnesium stearate and core tablets were compressed using suitable punch. The core tablets were coated with a dispersion of Methacrylate copolymer, mixed with talc.

The preparations being now on the market have several drawbacks. Due to the large amount of the excipients the tablet size is relatively large, and large tablets are difficult to swallow, especially for aged patients and uncooperative patients. Besides, due to the high excipient content the costs of materials of the manufacturing procedure are relatively high. The tablets according to the invention are of considerably smaller weight than the known tablets. Thus an improved therapeutical applicability has been achieved. Besides, the production of such tablets is more economical.

TABLE 1

Comparative Weight of Tablets Comprising Quetiapine Fumarate

| Product | Strength | | |
|---|---|---|---|
| | 200 mg | 300 mg | 400 mg |
| | Tablet weight | | |
| Reference | 610.0 mg | 820.0 mg | 890.0 mg |
| Test | 412.0 mg | 618.0 mg | 824.0 mg |

Reference: Seroquel XR of respective strengths
Test: Tablets prepared as per Example 1 of various strengths

DISSOLUTION

The in vitro specifications for generic products are established based on a dissolution profile. In the case of a generic drug product, the dissolution specifications are generally the same as the reference listed drug.

Dissolution was carried out for the first 5 hours in pH 4.8 buffer, followed by pH 6.6 phosphate buffer. The following compositions were tested: sustained release tablets comprising of 200 mg of Quetiapine fumarate, prepared according to example 1 as test and Seroquel XR® having quetaipine Fumarate 200 mg by Astrazeneca as reference.

The results obtained are summarized below in table 2.

TABLE 2

Dissolution profile of Quetiapine Fumarate
200 mg Sustained Release Tablets
(Example 1)

| Time (hrs) | Quetiapine Fumarate 200 mg Sustained Release Tablets |
|---|---|
| 0 | 0 |
| 2 | 16 |
| 4 | 37 |
| 6 | 56 |
| 8 | 73 |
| 12 | 86 |
| 20 | 92 |

The invention claimed is:

1. A sustained release dosage form consisting essentially of:
   Quetiapine or a pharmaceutically acceptable salt, polymorph, solvate, or hydrate thereof;
   one or more non-gellable release controlling polymer; and
   one or more pharmaceutically acceptable excipient(s).

2. The sustained release dosage form as in claim 1 wherein the dosage form comprises the drug in the matrix.

3. The sustained release dosage form as in claim 1 wherein the dosage form includes tablets, capsules, pellets, granules.

4. The sustained release dosage form as in claim 1 wherein the non-gellable release controlling polymer is selected from the group comprising cellulose acetate, acrylic polymer such as Poly (ethyl acrylate, methyl methacrylate) polymer, ammonio methacrylate copolymers.

5. The sustained release dosage form of claim 1, consisting of:
   Quetiapine or a pharmaceutically acceptable salt, polymorph, solvate, or hydrate thereof;
   one or more non-gellable release controlling polymers; and
   one or more pharmaceutically acceptable excipient(s).

\* \* \* \* \*